United States Patent
Prusik et al.

(10) Patent No.: US 7,161,023 B2
(45) Date of Patent: Jan. 9, 2007

(54) MORPHOLOGY CONTROL OF SUBSTITUTED DIACETYLENIC MONOMERS FOR SHELF LIFE MONITORING SYSTEMS

(75) Inventors: Thaddeus Prusik, Stroudsburg, PA (US); Dawn E. Smith, Martinsville, NJ (US); Ingo H. Leubner, Penfield, NY (US); Wesley A. Olmsted, Grafton, WI (US)

(73) Assignee: Temptime Corporation, Morris Plains, NJ (US)

( * ) Notice: Subject to any disclaimer, the term of this patent is extended or adjusted under 35 U.S.C. 154(b) by 348 days.

(21) Appl. No.: 10/900,448

(22) Filed: Jul. 28, 2004

(65) Prior Publication Data

US 2006/0025647 A1    Feb. 2, 2006

(51) Int. Cl.
*C07C 269/08* (2006.01)
*G01N 37/00* (2006.01)

(52) U.S. Cl. ......................... 560/158; 436/56
(58) Field of Classification Search ............... None
See application file for complete search history.

(56) References Cited

U.S. PATENT DOCUMENTS

| | | | | | |
|---|---|---|---|---|---|
| 3,999,946 | A | * | 12/1976 | Patel et al. | 422/56 |
| 4,189,399 | A | * | 2/1980 | Patel | 436/7 |
| 4,384,980 | A | * | 5/1983 | Patel | 436/58 |
| 4,788,151 | A | * | 11/1988 | Preziosi et al. | 436/2 |
| 4,789,637 | A | * | 12/1988 | Preziosi et al. | 436/2 |

* cited by examiner

*Primary Examiner*—Brian Davis
(74) *Attorney, Agent, or Firm*—Kirpatrick & Lockhart Nicholson Graham LLP (57) ABSTRACT

A system for recovering a diacetylenic monomer shelf life monitoring compound of reduced particle size and narrow size distribution range which comprises quenching a solution of the monomer by mixing the solution in a lower temperature quenching fluid having a base temperature which is at least about 30° C. below the nominal temperature at which the monomer compound recrystallizes from solution, the mixing being effected in such a manner as to limit the resulting quenching mixture temperature to one which is not higher than a maximum of about 15° C. above the quenching fluid base temperature.

12 Claims, 4 Drawing Sheets

MORPHOLOGY CONTROL OF SUBSTITUTED DIACETYLENIC MONOMERS FOR SHELF LIFE MONITORING SYSTEMS

BACKGROUND OF THE INVENTION

The present invention relates to systems, and elements, components, and compositions therefor, comprising substituted diacetylenic monomer components which are useful in monitoring and indicating the elapse of a predetermined integral of deleterious ambient conditions, such as time, temperature, humidity, actinic radiation, vaporous atmosphere, and the like, to which an associated product has been exposed and which thereby establish the shelf life of such a product. In particular, the invention provides means for economically preparing such monomer components as highly active, reduced-size particles which exhibit remarkable consistency over a narrow range of size distribution.

Typically, in monitoring the useful shelf life, i.e., the span of safe or potent utility, of a product of foodstuff, medicament, or the like which is known to be affected by, for example, a thermal ambient, an indicator system, often in the form of an affixed label, is associated with the product and exhibits a readily discernible property variation, such as a change of color or color density, at the end of the product's shelf life. To this end, such a system may comprise a thermally reactive composition appropriately formulated to provide such a color change response substantially concurrently with elapse of a given time-temperature integral commensurate with expiration of the product's predesignated shelf life. Of particular utility in such responsive compositions of shelf life monitoring systems are substituted diacetylenic monomer components which exhibit a distinct color change as a result of and generally concomitant with a solid state polymerization effected by changes in ambient conditions; for example, as in the case of a time-temperature indicator (TTI) system, an integral of time and temperature.

The distinct responses, e.g., color changes, of diacetylenic monomer components to thermal and other environmental stimuli provide bases for numerous highly functional and reliable monitoring system embodiments. One widely utilized type of such a system is implemented by incorporating a selected reactive monomer component into a composition formulated as a printable ink which is applied to a label capable of being associated, by adhesive layer or other means, with a target shelf life-limited product, such as an item of foodstuff or medicament. Selected to react in solid state polymerization to variant temperature ambients over a time period satisfying an integral matching the shelf life of the associated product, the diacetylenic component of an applied TTI label ink composition displays a predesignated color or color density signaling expiration of that shelf life.

Substituted diacetylenic monomers have been studied and utilized in shelf life monitoring systems for a substantial time. For instance, such utility of these numerous active monomers comprising at least two conjugated acetylene groups (—C≡C—C≡C—) and their unique physico-chemical properties, e.g., responsiveness to persistent temperature excursions by transforming into contrastingly colored solid state polymerization reaction products, have been described by Patel et al. (U.S. Pat. No. 3,999,946). The synthesis of these monomers and their incorporation into TTI and other shelf life indicator compositions are discussed there at length and continue to be useful in implementing embodiments of such systems. Also, the use of these diacetylenic monomer shelf life system components and improvements thereon, including broad ranges of substituents and complexes, and improved methods of monomer synthesis and blending in co-crystallization operations, have been described further by Patel (U.S. Pat. Nos. 4,189,399 and 4,384,980) and Preziosi et al. (U.S. Pat. Nos. 4,789,637 and 4,788,151). Such useful descriptions and examples of these diacetylenic monomer components finding application in shelf life monitoring systems to which the present invention relates are incorporated herein by reference. It should be noted that although the term "monomer" is used consistently throughout this specification with respect to the active monitor component materials, dimeric and polymeric component compounds of similar basic structure, as previously described in the cited references, are likewise to be considered included in this description.

As noted in the referenced specifications, numerous diacetylenic monomers may be synthesized to yield TTI components of widely varying reactive temperature ranges and resultant color densities. While such monomer components may generally be relied upon to exhibit reproducible results as indicators of shelf life end points, physical and morphological variables in these components, for example the size of their crystalline particles, often have a profound effect upon their response and performance in TTI and other monitoring applications. In addition, further requirements of crystal size limitation are often imposed by the ultimate utilization of the diacetylenic monomer composition, as in the need for sufficiently fine particles to enable formulation of a free-flowing printing ink.

Means for achieving such proper morphology, e.g., sufficiently small and uniform particle size, for diacetylenic monomer components of shelf life monitoring systems have heretofore been reliant, as described in the referenced art, upon expensive, low-efficiency intermediate operations for grinding or pulverizing these active materials. However, operations of this type not only are uneconomical, but they consistently degrade the monomer materials due to the unavoidable generation of heat, along with uncontrolled size reduction over the entire mass of monomer particles with a resultant excessive range of particle sizes.

There has thus existed for some time a need for a ready, reliable, and cost-effective means for achieving and controlling variation in reduced particle size active diacetylenic monomer components for use in TTI and other exposure integral monitoring systems without severely interrupting the system composition process by imposition of costly and inefficient grinding operations. The present invention obviates the noted shortcomings and disadvantages in the preparation of prior diacetylenic monomer component system products and provides means for readily and economically obtaining such monomer components within narrow ranges of desirably small particle sizes which have been shown to provide exceptionally consistent responsiveness in TTI and other such systems. The invention provides such diacetylenic monomer component products which comprise improved and highly effective shelf life systems while greatly reducing costs and achieving significant savings in time and material resources during system formulation.

SUMMARY OF THE INVENTION

For use in the preparation of a desired shelf life monitoring system, for instance a TTI device, a substituted diacetylenic monomer of predetermined time-temperature integral may be synthesized as described in the referenced patent specifications by appropriate selection and balance of various parameters, such as precursor acetylenic condensate constituents or substituted variants thereof, conditions of synthesis, matching of components for co-crystallized compositions, and the like. The resulting compound is then initially recovered from the reactant solution as a crude form of the diacetylenic monomer by common crystallization means, such as evaporation, sublimation, solution cooling, or selective salvation.

The crude crystalline monomer may be retained in that form until processed during formulation of the ultimate TTI composition or it may be purified further by dissolution and recrystallization. Previous means for the latter operation have typically comprised batch cooling of monomer solution from a dissolution temperature of about 90 to 100° C. to a temperature below that sufficient for recrystallization of the monomer compound, either by immersion of the solution vessel in an external bath of coolant or by rapid introduction of the monomer solution directly into a body of quenching fluid exhibiting limited solvency for the monomer, due either to its inherent chemical composition or its low temperature. Diacetylenic monomer treated in either manner is normally recovered, after washing, filtration, and drying, as a crystalline product having a wide range of particle sizes, comprising both individual and agglomerate particles. A significant portion of such recrystallized monomer product has a particle size well in excess of the 10 µm range which is preferred in compounding shelf life monitoring system compositions, such as inks for label devices or the like.

The morphology of the recovered diacetylenic monomer also influences the performance of the incorporating monitor compositions in that the consistency of response exhibited by TTI and other shelf life monitoring systems have been observed to be affected in significant measure by the sizes and size distributions of the incorporated diacetylenic monomer particles. Investigations into the behavior of active component diacetylenic monomers have indicated improved consistency of indicator results when their reduced crystalline particle sizes are constrained within narrow ranges.

In order to prepare an effective TTI ink composition comprising a diacetylenic monomer component obtained in the foregoing manner, it previously has been necessary to subject the composition materials, particularly the monomer, to a comminution operation, typically by milling the ink composition, such as with rollers, balls, or high-speed shearing apparatus. Although size reduction is generally achieved, a wide range of monomer particle size distribution and related instability in TTI composition response continue to be prevalent. Further, a significant disadvantage of milling or grinding operations, i.e., heat generation, has been seen to result in premature color-shift polymerization of many of the diacetylenic monomer materials.

With a goal of achieving a reduction of monomer particle size into the preferred range of about 10 µm without resort to deleterious grinding, investigations resulting in the present invention undertook a variety of procedures for recrystallization of synthesized diacetylenic monomer from heated purification solution. One such procedure providing particularly good results comprised quenching the heated monomer solution by introduction into a low-temperature, miscible quenching fluid in such a manner as to achieve and maintain a rapid temperature decrease of the resulting fluid mixture into a maximum range of preferably about 10 to 15° C. which is at least about 30° C. below the nominal monomer recrystallization temperature, i.e., the temperature at which the monomer normally exhibits significant recrystallization from the solution as a result of moderate external bath cooling. Surprisingly, not only did such rapid cooling result in a decrease of the mean particle size of the recrystallized monomer into a range approaching the preferred 10 µm, but the range of particle size distribution narrowed significantly with resulting improvement in consistency of indicator performance, as earlier noted.

A first embodiment of the invention devised to meet the noted parameters for the improved, controlled recrystallization process comprises introducing the monomer solution at a temperature sufficient to ensure complete dissolution of the monomer, e.g., about 95° C., intermittently and with substantial agitation into a quenching fluid having a maximum temperature at least about 35° C. below the nominal monomer recrystallization temperature. For this purpose, the monomer solution is introduced into a quenching fluid having a base temperature preferably about 50° C. below the nominal recrystallization temperature in such portions as to ensure that the temperature of the quenching mixture of quenching fluid and monomer solution is not increased above the upper limit of the preferred temperature range. Contemporaneous external cooling of the quenching mixture enables the lower range temperature to be recovered rapidly between periods of monomer solution introduction and ensures that the noted parameters are readily satisfied. The extent of such contemporaneous cooling may be utilized to establish the frequency and volume of the monomer solution introductions.

In a second embodiment, the monomer solution may be introduced continuously, normally with substantial agitation, into the miscible quenching fluid at a rate, dependent upon the volume of the quenching fluid and the extent of contemporaneous cooling, which will maintain the specified quenching temperature range. In yet another embodiment, the quenching fluid and monomer solution may be continuously introduced contemporaneously into a mixing site, e.g., an externally cooled vessel or a conduit leading directly to filtration or other recrystallized monomer compound recovery apparatus, at such respective rates as will maintain the noted recrystallization temperature range. Such an in-line process thus enables continuous recovery of recrystallized monomer, if desired.

BRIEF DESCRIPTION OF THE DRAWING

The present invention will be described with reference to the accompanying drawing of which.

DESCRIPTION OF THE INVENTION

The manner of implementation and use of the present invention to achieve the noted advantages may be readily seen by reference to the following exemplary descriptions. Although these examples reflect, as a matter of practicality, the use of a limited number of active diacetylenic monomer compounds, the desirable effects of the novel processing may be achieved with numerous of these useful components of shelf life monitoring compositions.

EXAMPLE I

In order to provide a source of active diacetylenic monomer component to be used as exemplary material in the context of the present invention, a stock composition of a preferred monomer, 2,4-hexadiyn-1,6-bis (ethylurea), dubbed "KE" by a major user in the marketplace, was prepared in a synthesis comprising the reaction of monopropargylamine and ethylisocyanate as described in the above-cited references, e.g., U.S. Pat. No. 4,788,151. As in a final stage of the described synthesis process, the crude crystalline KE monomer was recovered and purified from an acetic acid solution by cooling at a moderate rate from about 100° C. to about 20° C. in a recrystallization vessel set in an external water bath. In the course of the gradual cooling, a significant amount of recrystallized monomer product appeared at about 45° C., a temperature which could be deemed the aforementioned "nominal" recrystallization temperature for this monomer material.

The recrystallized stock monomer product when examined by optical microscopy exhibited complex crystalline structures with fragmented and agglomerated particles having a broad estimated size distribution over a range of about 40 μm to 80 μm. Although such microscopic examination may be initially employed with monomer examples in order to effect general size comparisons and assess aspects of morphology, the preferred and more reliable means of obtaining characteristic particle size specifications utilized Lasentec Particle Sizer instrumentation which provides automated statistical analysis and chord size specifications based on well-known Focused Beam Reflection Method (FBRM) measurements. Therefore, in the following examples monomer particle size characterizations will primarily reflect the mean particle sizes in chord length, i.e., a statistical average of all longitudinal and transverse axes, rather than particle diameter. Recorded data may also include particle size distribution values of $C_{10}$, $C_{50}$, and $C_{90}$, indicating the maximum chord lengths for 10%, 50%, and 90% of the particles, and the Decade Ratio $C_{90}/C_{10}$ which provides an indication of the depth of particle size distribution range. When characterized under these preferred criteria, the foregoing stock KE monomer, 2,4-hexadiyn-1,6-bis (ethylurea), prepared by the earlier gradual cooling recrystallization method exhibited a particle size mean chord length of 24.4 μm.

EXAMPLE II

In the interest of ease of manufacture and more rapid recovery of recrystallized diacetylenic monomers, earlier recrystallized processing of these materials employed, in lieu of solely external bath or jacket cooling, a quenching operation in which about 3 parts by weight (Note: compositions and component ratios are presented throughout this description on a weight basis, unless otherwise specified) of a solution of near monomer solute saturation, e.g., about 10% of crystalline KE monomer in acetic acid at about 95° C., were mixed with rapid stirring agitation into a body of about one part of methanol at initial ambient air temperature of about 20° C. The methanol quenching fluid is substantially a non-solvent for the monomer at the lower quenching temperatures. After filtration, washing sequentially with methanol and acetone, and air-drying, recovery of recrystallized KE monomer was generally about 80% to 85%. Recovered monomer is normally stored under refrigeration until ultimate use.

The foregoing manufacturing process was reproduced on a laboratory scale employing the stock KE monomer of Example I in order, in particular, to more closely observe the quenching operation and to characterize and evaluate the resulting crystalline product. During quenching in a polyethylene vessel, the temperature of the recrystallization fluid mixture, i.e., the methanol and increasing proportions of intermixed monomer solution, rose from the 20° C. ambient to about 70° C. before returning to ambient, a temperature range of about 50° C. during recrystallization. The recovered recrystallized KE monomer exhibited a smaller mean chord particle size, vis-à-vis the stock product, of 22.9 μm, which was, however, well above the 10 μm range desired for pulverization-free utilization, although the $C_{50}$ of 16.2 μm and a Decade Ratio of 15.0 also showed some improvement over the stock KE monomer.

EXAMPLE III

To gain further insight into whether the recrystallized monomer particles might be sufficiently reduced in size by lowering the temperature of the quenching fluid, Example II was repeated with the exception that the methanol in the quenching vessel was cooled to about 0° C. in an external circulating ice-water bath prior to introduction of the KE monomer solution. Over the course of the quenching recrystallization period, the fluid mixture temperature rose to about 65° C. Despite the significantly lower initial recrystallization temperature, the mean recovered particle size of 24.7 μm varied little from the stock material, while the size distribution suggested by the Decade Ratio of 14.8 varied only minimally from that exhibited in the material of Example II.

EXAMPLE IV

The temperature of the methanol quenching fluid was lowered further to about −12° C. in a repeat of Example III employing an external dry ice-acetone bath. The recrystallization mixture finalized in temperature at about 63° C. after a rise of about 75° C., and the mean particle size and size distribution range of the recovered crystalline KE monomer exhibited a reversion to the excessive values of 25.1 μm and Decade Ratio of 16.0.

EXAMPLE V

In a yet more aggressive attempt to achieve a beneficial reduction in recrystallized monomer particle size and distribution range, Example IV was repeated with methanol quenching fluid chilled to about −25° C. in an external bath of acetone and a greater amount of dry ice. The KE monomer recrystallization was continued to a stabilized temperature of about 59° C. after an increase of about 85° C. with some significant reduction of mean particle size to 17.8 μm. This particle size remained too great to enable use of the recrystallized monomer directly, i.e., without grinding or pulverizing, in a TTI monitor ink composition. Further, the Decade Ratio of 16.6 for the recovered particles indicated a less desirable size distribution than previously obtained. A comparison of the Ratios from the foregoing exemplary results suggested that the range of particle size distribution follows the magnitude of temperature increase in the recrystallization fluid mixture during the quenching operation.

Although decrease of initial quenching fluid temperature, even to the extremes indicated in the above examples, in practice of the prior art quenching recrystallization process failed to yield recovered monomer particles of sufficiently reduced size for direct incorporation into printed shelf life monitor compositions, there appeared a trend in that direction with each of the $C_{10}$, $C_{50}$, and $C_{90}$ chord lengths decreasing as the initial quenching temperatures decreased. Further attempts to achieve significant particle size reductions in this manner and to obviate the apparent deleterious effects on size distribution range of large excursions in recrystallizing mixture temperatures led surprisingly to the discoveries underlying the present invention, namely that the desired reduction in particle size and a uniformly narrow range of particle size distribution are influenced in significant measure not only by an initial low quenching fluid temperature, but also by the maintaining of a consistently narrow range of such low temperature throughout the recrystallization operation.

In one embodiment of the present invention, the requisite narrow range of low quenching temperature is maintained by limiting the amount of hot monomer solution which is introduced at one time into a bath-chilled body of quenching fluid to such an amount as will not raise the recrystallization mixture temperature above the upper limit of the desired range. The amount of solution to be introduced in this manner may readily be determined depending upon extant variables, such as the initial temperature of the quenching fluid and the efficiency of the quenching mixture cooling system, i.e., the material and contact area of the quenching vessel and the external cooling medium temperature. In this embodiment, increased amounts of recrystallized monomer within the initial particle size ranges may be recovered during the process simply by introduction of additional similar portions of monomer solution to the resulting quenching mixture, provided that the range of quenching temperature is substantially maintained during each additional batch operation.

EXAMPLE VI

In a representative example of the foregoing embodiment of the invention, the materials of Example III were employed in the following manner. While rapid agitation was continued throughout the processing in both the quenching vessel and ice-water bath, about one part of the 95° C. KE monomer solution was introduced at once into about four parts of the 0° C. methanol quenching fluid, a ratio predetermined by caloric balance calculation to limit the rise in quenching fluid temperature to a maximum of about 15° C. Immediate recrystallization of the dissolved monomer was apparent and continued while the mixture was allowed to cool to the initial quenching temperature of about 0° C.

A sample of recrystallized KE monomer was characterized by FBRM analysis which revealed the significant improvement achieved by the invention as reflected in the reduction of mean chord length to 13.0 μm with a $C_{50}$ of 9.0 μm and a Decade Ratio of 12.1, indicating a substantial narrowing of the range of monomer particle sizes to that approximating the 10 μm size desired for direct inclusion of the recovered monomer into a TTI monitor ink composition.

A second similar portion of the heated monomer solution was added to the quenching vessel, and the re-warmed fluid mixture was allowed to return to about 0° C. with further recrystallization of the dissolved KE monomer. The quenching operation was repeated with additional like portions of monomer solution prior to normal crystalline monomer recovery operations.

Figure 1:
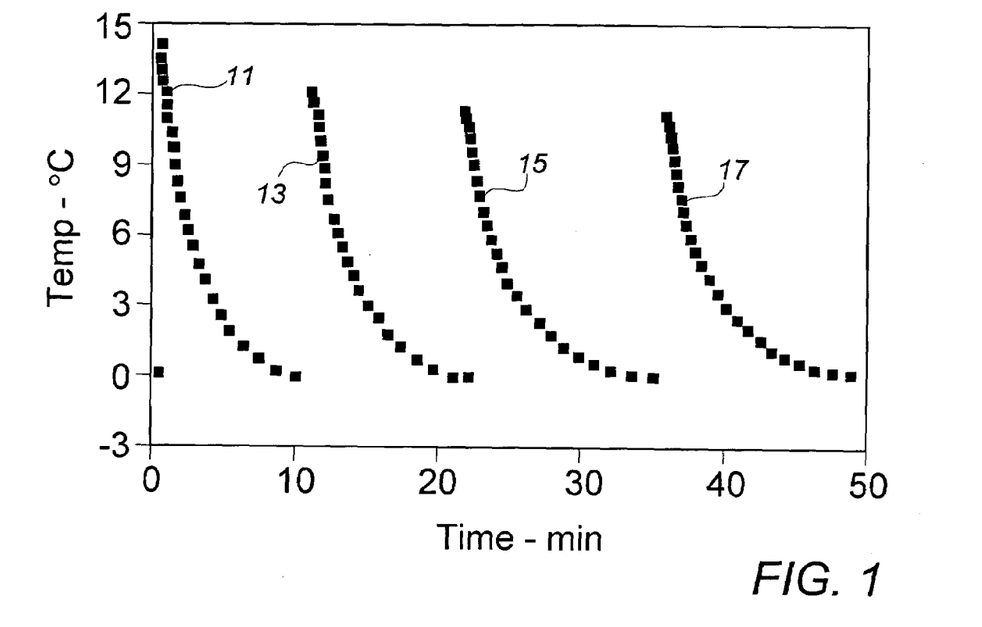
FIG. 1 depicts the quenching temperature profile of an implementation of a first embodiment of the invention.

As depicted in FIG. 1, during the foregoing processing, the temperature of the mixture of quenching methanol and monomer solution immediately rose from the initial 0° C. to about 15° C., the maximum temperature increase predetermined for the calculated amount of introduced monomer solution. In response to the cooling effected by the external bath, after the first addition of monomer solution the mixture temperature returned to the datum of about 0° C. in about 10 min, as shown at profile 11 of FIG. 1. The subsequent additions of monomer solution provided similar responses, as in profiles 13, 15, 17, with each return to datum temperature requiring somewhat more time due to the increase in accumulated mass of recrystallization quenching mixture. Analysis of the recovered KE monomer confirmed the outstanding improvement in particle size and size distribution observed in the initial sampling.

EXAMPLE VII

Figure 2:
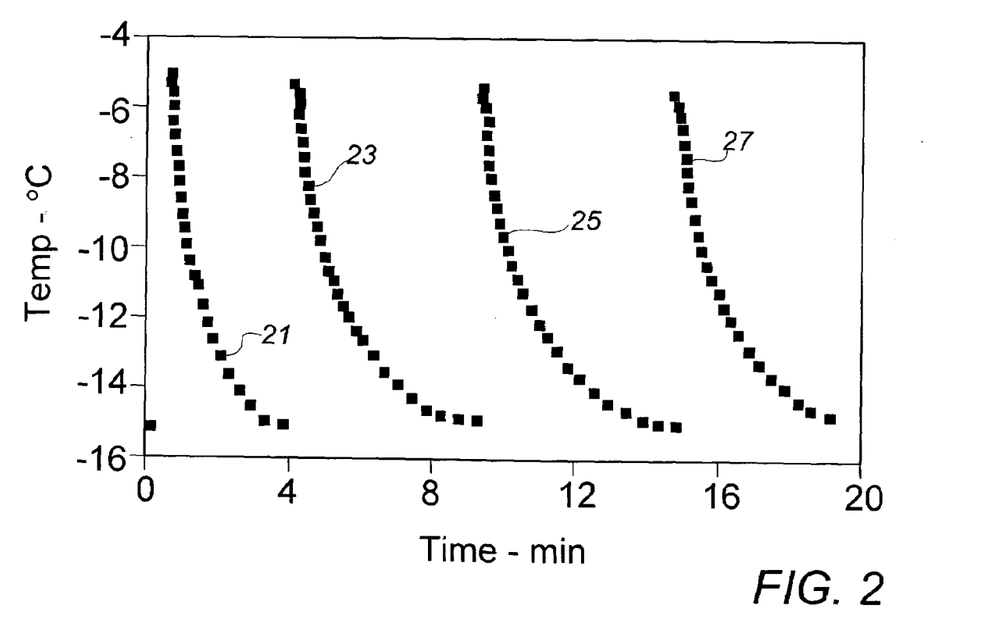
FIG. 2 depicts the quenching temperature profile of another implementation of a first embodiment of the invention.

A similar application of this embodiment of the invention was utilized with materials of Example IV. The external dry ice-acetone cooling bath was adjusted to reduce the base temperature of the methanol quenching fluid to about −15° C., and the 95° C. KE monomer solution was introduced at once into the quenching vessel at a ratio of about one part to about eight parts of methanol. The recrystallization mixture temperature increased by about 10° C. to the precalculated maximum of about −5° C. with recrystallization of the KE monomer continuing during re-cooling of the mixture, depicted as profile 21 in FIG. 2, to the initial temperature of about −15° C. Subsequent introductions of like amounts of monomer solution resulted in substantially similar responses of quenching mixture temperature cycling, varying only slightly in each cycle profile 23, 25, 27, due to increasing mass of fluid mixture. The cycling quenching temperature nonetheless remained within the predetermined range, not exceeding the span of about 10° C. as depicted in FIG. 2.

Characterizing analysis of the recrystallized KE monomer revealed a further improved reduction of the mean particle size to a chord length of 12.0 μm with a $C_{50}$ of 8.4 μm and a Decade Ratio of 11.7.

EXAMPLE VIII

Figure 3:
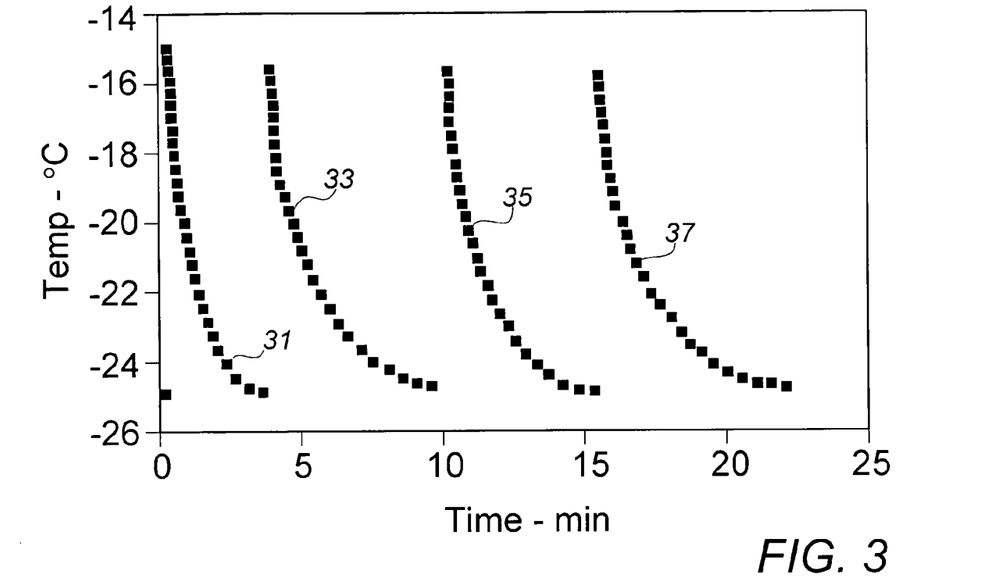
FIG. 3 depicts the quenching temperature profile of yet another implementation of a first embodiment of the invention.

The procedures of Example VII were repeated with the more severely chilled external dry ice-acetone bath temperature of about −25° C. employed in Example V. Recrystallization of the KE monomer occurred upon multiple monomer solution additions with temperatures remaining, as shown in FIG. 3 at depicted cooling profiles 31, 33, 35, 37, within the 10° C. pre-specified cycling range up to the pre-calculated maximum of about −15° C. Analysis of the recovered monomer confirmed yet further particle size reduction, exhibiting a mean chord length of 11.6 μm and a $C_{50}$ of 8.4 μm with a Decade Ratio of 10.7.

Further investigations generally following the procedures of the foregoing exemplary implementations of the outlined embodiment of the invention, particularly including variations in quenching mixture temperature range, as dependent, for example, upon calculated combinations of initial quenching temperature and ratios of KE solution and quenching fluid, provided an indication of the useful range of those parameters in practice. Considering about 45° C. as the above-noted nominal recrystallization temperature datum for KE diacetylenic monomer in a moderate solvent capable of dissolving at least about 10–15% monomer, the maximum temperature for the quenching fluid may be selected to be at least about 30° C. below the nominal datum, preferably having an initial temperature of at least about 45° C., more preferably about 70° C., below that datum temperature. Throughout the term of processing the quenching mixture temperature remains within a range of not more than about 15° C. above the initial temperature, which is normally determined by the external cooling means.

A second embodiment of the invention may be implemented by introducing the heated monomer solution into the quenching fluid continuously, rather than in recurrent batches as in the above first embodiment, at a rate which does not raise the temperature of the quenching mixture to a level which exceeds the upper limit of the preferred range during a given quenching period. As with the earlier embodiment, the appropriate addition rate of monomer solution may be calculated from a heat transfer balance based upon the rate at which the quenching mixture is cooled by the external cooling means. This calculation takes into account, as before, such predetermined variables as the initial temperature of the quenching fluid and the efficiency of the quenching mixture cooling system, i.e., the material and contact area of the quenching vessel, and the cooling medium temperature.

EXAMPLE IX

Figure 4:
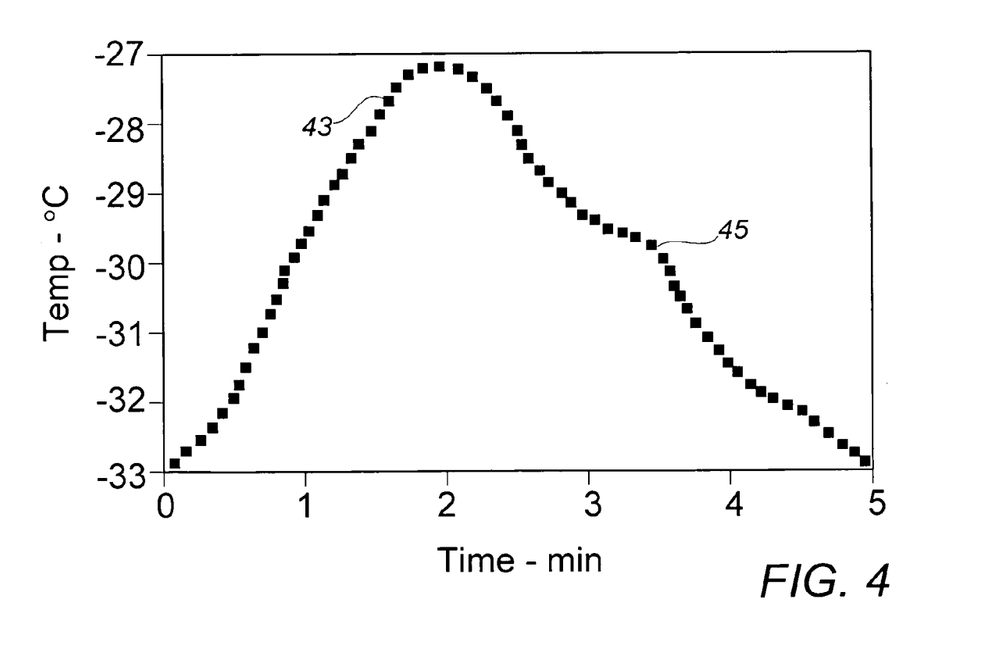
FIG. 4 depicts the quenching temperature profile of an implementation of a second embodiment of the invention.

A methanol quenching fluid was chilled to about −33° C. in an external dry ice-acetone bath in substantially the manner of the foregoing examples, with the exception that the quenching vessel was of stainless steel, thereby providing for a more rapid response to external coolant than was available with the previously employed polyolefin vessel. A 95° C. solution of 10% KE in acetic acid was introduced into the quenching vessel at a constant rate which was initially about one part/min per 12 parts of quenching fluid. As depicted in FIG. 4, the quenching mixture temperature increased to about −27° C. after about 2 minutes of monomer solution addition at which time more dry ice was added to the bath, as at 43, to reduce its temperature to about −45° C. and prevent further increase in the range of quenching mixture temperature. During further addition of monomer solution over about 3 minutes, with additional bath coolant added at 45, the quenching mixture temperature returned to the initial −33° C. range. In this aspect of the invention, maintenance of a desired narrow quenching mixture temperature range of about 6° C. was thus achieved during constant rate monomer solution feed by controlled variation of the temperature of the coolant bath.

When recovered in the usual manner, the recrystallized KE particles were characterized by FBRM analysis as having mean chord length of 10.8 μm with a $C_{50}$ of 6.7 μm and a Decade Ratio of 12.1, indicating a range of monomer particle sizes sufficiently approximating the target 10 μm size to be useful for direct inclusion into a TTI monitor ink composition.

EXAMPLE X

Figure 5:
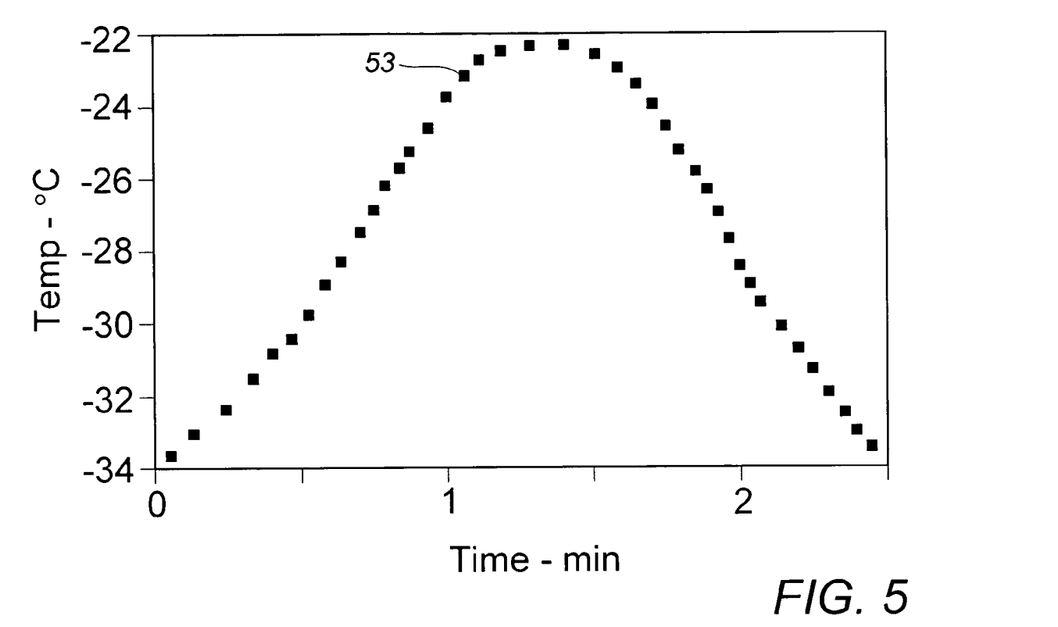
FIG. 5 depicts the quenching temperature profile of another implementation of a second embodiment of the invention.

The steel quenching vessel of Example IX was employed once again while, in this implementation of the invention, the external bath was maintained at about −50° C. After an initial introduction, the 95° C. solution of 10% KE in acetic acid was pump-fed into the methanol quenching mixture at a constant but more rapid rate of about one part/min per 4 parts. As shown in FIG. 5, the temperature of the quenching mixture increased toward the upper limit of the desired 10° C. quenching range where, at 53, the monomer solution feed was terminated, thereby allowing the quenching mixture to cool rapidly toward the initial mixture temperature. This exemplary operation thus utilized the option presented by the invention of controlling the recrystallization temperature range by means of the combination of constant external bath temperature and variation of monomer solution feed rate. The recrystallized KE particles exhibited a mean chord length of 11.7 μm with a $C_{50}$ of 7.3 μm and a Decade Ratio of 13.2, the latter property reflecting the broader recrystallization temperature range.

EXAMPLE XI

Further investigations of the efficacy of the invention were conducted utilizing the previously described embodiment, that is, maintaining the desired recrystallization temperature range by means of the more readily controllable variations in monomer solution feed rate vis-à-vis bath temperature control. Additional parameter variants were also employed in this exemplary procedure, namely, the use of a glass quenching vessel instead of steel, and substitution of dimethyl formamide (DMF) for both the monomer solvent and the initial quenching fluid, thus providing a process fluid of lower melting point. The greater solvency of the DMF over the previous methanol as a quenching fluid presented no apparent disadvantages at the low temperature range, based on an external bath temperature of about −27° C., in which the processing was conducted.

Figure 6:
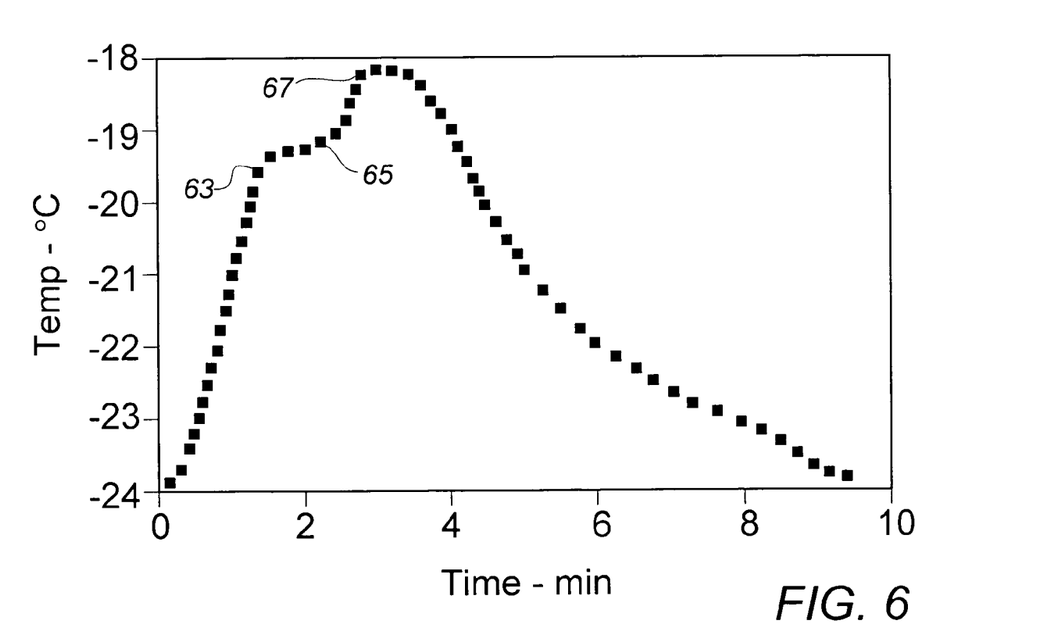
FIG. 6 depicts the quenching temperature profile of yet another implementation of a second embodiment of the invention.

A 95° C. solution of 10% KE in DMF was introduced into the DMF quenching fluid of about −24° C. at a rate of about one part/min per 6 parts of quenching fluid. As depicted in the profile of FIG. 6, the quenching mixture temperature increased to about −20° C. after about one minute of monomer solution addition at which time the monomer solution feed was interrupted, as at 63, to prevent further increase in the range of quenching mixture temperature. After about 0.5 minute, the feed of monomer solution was resumed, as at 65, for an additional 0.5 minute with further increase in quenching temperature to about −18° C. where, at 67, monomer solution feed was terminated in order to prevent quenching mixture excursion beyond the desired 6° C. range and to allow the mixture to return to the lower range limit of about −24° C.

The recrystallized KE particles obtained from this narrow range temperature controlled feed process embodiment exhibited extraordinary particle size limits, viz., a mean chord length of 9.4 μm with a $C_{50}$ of 6.3 μm and a Decade Ratio of 9.4, each more than sufficient to meet the 10 μm size range required for direct inclusion into a TTI monitor ink composition.

EXAMPLE XII

Figure 7:
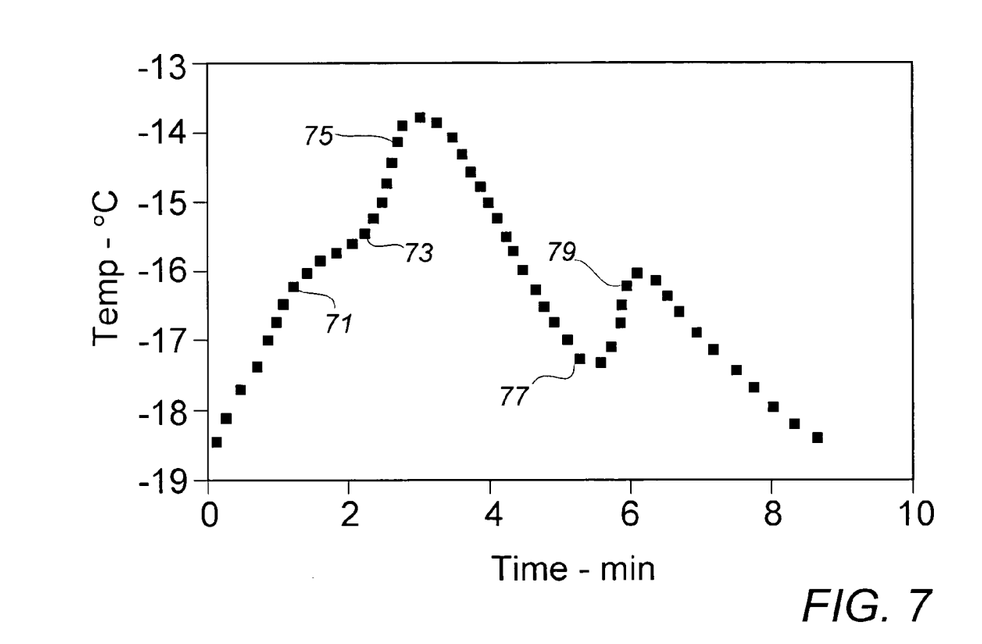
FIG. 7 depicts the quenching temperature profile of a still further implementation of a second embodiment of the invention.

This example of the versatility of the invention employed the DMF monomer solution and quenching fluid of Example XI with closer feed control at a higher feed rate of about one part/min per 3.5 parts of quenching fluid to limit the somewhat higher quenching temperature range to about 5° C. As depicted in FIG. 7, the feed of 95° C. KE solution in DMF began at a quenching mixture temperature of about −19° C. which increased to a point of feed interruption, at 71, to slow the temperature gain at about −16° C. Feed was resumed, at 73, about 0.5 minute later and was interrupted again, at 75, when the mixture temperature approached the selected range maximum of about −14° C. The quenching mixture temperature was allowed to return to the lower region of the range where the monomer solution feed was resumed, at 77, resulting in mixture temperature increase to about mid-range where, at 79, feed was terminated to allow the quenching mixture temperature to return to the range minimum of about −19° C. FBRM analysis characterized the recovered recrystallized KE particles as being substantially within the same desired size and size range as those obtained in Example XI.

EXAMPLE XIII

Figure 8:
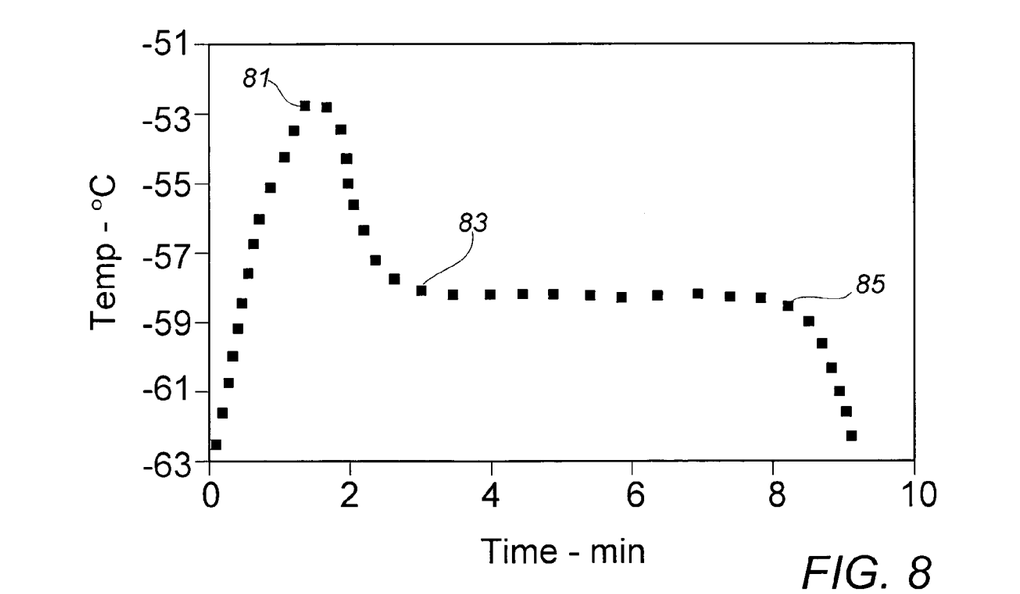
FIG. 8 depicts the quenching temperature profile of an additional implementation of a second embodiment of the invention.

A further variation in processing parameters in the present invention embodiment again provided desired monomer particle recrystallization. In the current example, a 95° C. solution of KE monomer in DMF was introduced at a rate of about one part/min per 6 parts of methanol at about −62° C. in a steel vessel chilled in a dry ice-acetone bath of about −70° to −75° C. The projected thermal balance at the quenching vessel was more closely calculated in this example than in the earlier implementations and the results led to the selected feed rate and bath temperature parameters. As can be seen in FIG. 8, the addition of KE monomer solution initially prompted an increase in quenching mixture temperature to the selected maximum of about −53° C., as at 81. By that time the coolant bath had dropped to about −75° C. which sufficiently overcame the heat input from added monomer solution to effect cooling of the quenching mixture to about −58° C., as at 83. From that point, the established thermal transfer balance continued until termination of monomer solution addition, at 85. The recovered recrystallized KE monomer particles exhibited near target size and size range characterizations of 13.1 μm mean chord length with a $C_{50}$ of 9.3 μm and a Decade Ratio of 12.0. This example was particularly significant in confirming the relative ease with which the invention process could be resolved to constant rate commercial production by implementation of simple temperature feed-back and monomer solution input control instrumentation.

A number of the foregoing exemplary implementations of the present invention repeated with other commercially available and preferred diacetylenic monomer compounds described in the above-incorporated references, such as 2,4-hexadiyn-1,6-bis (propylurea), a 2:1 co-crystallization of 2,4-hexadiyn-1,6-bis (ethylurea) and 2,4-hexadiyn-1,6-bis (propylurea), or a co-crystallized mixture of asymmetric synthesis comprising 2,4-hexadiyn-1-ethylurea-6-propylurea, provided substantially similar improvements in active shelf life monitoring system compositions.

It is anticipated that other embodiments and variations of the present invention will become readily apparent to the skilled artisan in the light of the foregoing description and examples, and such embodiments and variations are intended to likewise be included within the scope of the invention as set out in the appended claims.

What is claimed is:

1. A process for recovering a diacetylenic monomer compound which comprises effecting recrystallization of said monomer compound by means of quenching a heated solution thereof in a lower temperature miscible quenching fluid characterized in that
    a) said quenching fluid is initially cooled to a base temperature which is at least about 30° C. below a nominal temperature at which said monomer compound recrystallizes from the solution; and
    b) said monomer solution is mixed with said cooled quenching fluid in such a manner as to limit the resulting quenching mixture temperature to one which is not higher than a maximum of about 15° C. above said base temperature,
thereby achieving recrystallization of said monomer compound as particles of reduced size having a narrow range of size distribution.

2. A process according to claim 1 characterized in that
    a) said quenching fluid is contained in an externally cooled quenching vessel;
    b) a first portion of said monomer solution is mixed into said quenching fluid in an amount which is insufficient to increase the temperature of said resulting quenching mixture above said maximum temperature;
    c) said resulting quenching mixture is cooled in said quenching vessel; and
    d) a subsequent portion of said monomer solution is mixed into said resulting quenching mixture in an amount which is insufficient to increase the temperature of the accumulated quenching mixture above said maximum temperature.

3. A process according to claim 2 wherein additional subsequent steps of cooling and mixing are effected.

4. A process according to claim 2 wherein said monomer compound is 2,4-hexadiyn-1,6-bis (ethylurea), said base temperature is about 0° C., and said maximum temperature is about 15° C.

5. A process according to claim 2 wherein said monomer compound is 2,4-hexadiyn-1,6-bis (ethylurea), said base temperature is about −15° C., and said maximum temperature is about −5° C.

6. A process according to claim 2 wherein said monomer compound is 2,4-hexadiyn-1,6-bis (ethylurea), said base temperature is about −25° C., and said maximum temperature is about −15° C.

7. A process according to claim 1 characterized in that
    a) said quenching fluid is contained in an externally cooled quenching vessel; and
    b) said monomer solution is mixed into said quenching fluid at a rate which is insufficient to increase the temperature of the accumulating quenching mixture above said maximum temperature.

8. A process according to claim 1 characterized in that
    a) said quenching fluid is contained in an externally cooled quenching vessel;
    b) said monomer solution is mixed into said quenching fluid at a substantially constant rate; and
    c) said quenching vessel is cooled at a rate which is sufficient to prevent the temperature of the accumulating quenching mixture from increasing above said maximum temperature.

9. A process according to claim 8 wherein said monomer compound is selected from the group consisting of 2,4-hexadiyn-1,6-bis (ethylurea), 2,4-hexadiyn-1,6-bis (propylurea), a 2:1 co-crystallization of 2,4-hexadiyn-1,6-bis (ethylurea) and 2,4-hexadiyn-1,6-bis (propylurea), and a co-crystallized mixture of asymmetric synthesis comprising 2,4-hexadiyn-1-ethylurea-6-propylurea.

10. A process according to claim 1 characterized in that
   a) said monomer solution and said quenching fluid are contemporaneously introduced into and mixed in an externally cooled quenching vessel; and
   b) said quenching vessel is cooled at a rate which is sufficient to prevent the temperature of the accumulating quenching mixture from increasing above said maximum temperature.

11. A process according to claim 1 characterized in that
   a) said monomer solution and said quenching fluid are contemporaneously delivered to a mixing site at respective rates which ensure that said maximum quenching mixture temperature is not exceeded.

12. A process according to claim 11 wherein said quenching mixture is delivered to a recrystallized monomer compound recovery apparatus.

* * * * *